United States Patent
Khandelwal et al.

(10) Patent No.: US 6,783,772 B1
(45) Date of Patent: Aug. 31, 2004

(54) PHARMACEUTICAL PREPARATIONS CONTAINING ALENDRONATE SODIUM

(76) Inventors: Sanjeev Khandelwal, Prem Nivas, 13, Altamount Road, Mumbai (IN), 400026; Pratibha Omray, 501, Redwoods, Vasant Garden, (West) Mulund § Mumbai (IN), 400080

( * ) Notice: Subject to any disclaimer, the term of this patent is extended or adjusted under 35 U.S.C. 154(b) by 0 days.

(21) Appl. No.: 10/734,531

(22) Filed: Dec. 12, 2003

(51) Int. Cl.$^7$ .............................. A61K 9/14; A61K 9/20; A61K 9/22; A61K 9/24; A61K 9/26
(52) U.S. Cl. ....................... 424/465; 424/464; 424/468; 424/469; 424/471; 424/172; 424/484; 424/488
(58) Field of Search ................................ 424/464, 465, 424/468, 469, 484, 471, 472, 488

(56) References Cited

U.S. PATENT DOCUMENTS

| | | | | |
|---|---|---|---|---|
| 5,358,941 A | * | 10/1994 | Bechard et al. ............. | 514/102 |
| 6,248,363 B1 | * | 6/2001 | Patel et al. ................. | 424/497 |
| 6,350,471 B1 | * | 2/2002 | Seth ........................... | 424/480 |
| 6,476,006 B2 | * | 11/2002 | Flashner-Barak et al. ..... | 514/76 |
| 6,676,965 B1 | * | 1/2004 | Lulla et al. ................. | 424/458 |
| 2003/0091623 A1 | * | 5/2003 | Cumming et al. .......... | 424/465 |
| 2003/0133982 A1 | * | 7/2003 | Heimlich et al. ........... | 424/469 |

* cited by examiner

Primary Examiner—Thurman K. Page
Assistant Examiner—S. Tran
(74) Attorney, Agent, or Firm—Muserlian, Lucas and Mercanti

(57) ABSTRACT

An oral composition in tablet form containing therapeutic amounts of alendronate sodium for release of the alendronate sodium in the stomach and by passing the oesophagus, comprising a compacted granulated core with the alendronate sodium embedded in an inert fiber matrix, lined with a moisture barrier film and enclosed in a sugar based inert fiber matrix shell.

2 Claims, No Drawings

PHARMACEUTICAL PREPARATIONS CONTAINING ALENDRONATE SODIUM

This invention relates to pharmaceutical preparations. In particular, this invention relates to pharmaceutical preparations containing alendronate sodium.

Alendronate sodium is a white, crystalline, non-hygroscopic powder. It is soluble in water, very slightly soluble in alcohol, and practically insoluble in chloroform. Typically, alendronate sodium Tablets for oral administration contain either 6.53, 13.05 mg or 52.21 mg of alendronate monosodium salt trihydrate, which is the molar equivalent of 5.0, 10.0 mg and 40.0 mg, respectively, of free acid, and the typically, the following inactive ingredients: microcrystalline cellulose, anhydrous lactose, croscarmellose sodium, and magnesium stearate.

Alendronate sodium belongs to a class of chemical compounds known as Bisphosphonates, which are synthetic analogs of pyrophosphate that binds to bone hydroxyapatite. Alendronate sodium is chemically described as (4-amino-1-hydroxybutylidene) bisphosphonic acid monosodium salt trihydrate. The empirical formula of alendronate sodium is $C_4H_{12}NNaO_7P_2.3H_2O$ and its formula weight is 325.12. Alendronate sodium is therefore an aminobisphosphonate that acts on osteoclasts, the bone-resorbing cells. Alendronate inhibits bone resorption with no direct effect on bone formation, although the latter process is ultimately reduced because bone resorption and formation are coupled during bone turnover. Alendronate sodium thus reduces the elevated rate of bone turnover observed in postmenopausal women to the levels found in premenopausal women. As a specific inhibitor of osteoclast-mediated bone resorption. Overall therefore alendronate Sodium reduces the amount of calcium lost from bones and increases the density of bones.

Normally bones are being rebuilt all the time. First, old bone is removed (resorbed). Then a similar amount of new bone is formed. This balanced process keeps the skeleton healthy and strong.

Osteoporosis is a condition that strikes postmenopausal women as a result of estrogen withdrawal and the consequential depletion of calcium via the kidneys, which is hitherto retained by the mechanism of estrogen and the phosphorus calcium ion exchange mechanism. Osteoporosis causes a thinning and weakening of the bones. It is common in women after menopause. Menopause happens when the ovaries stop producing the female hormone, estrogen, or is removed (which may occur, for example, at the time of a hysterectomy). After menopause, bone is removed faster than it is formed, so bone loss occurs and bones become weaker. Therefore, maintaining bone mass is important to keep bones healthy.

In Postmenopausal Women, therefore osteoporosis is characterized by low bone mass that leads to an increased risk of fracture. The diagnosis can be confirmed by the finding of low bone mass, evidence of fracture on x-ray, a history of osteoporotic fracture, or height loss or kyphosis, indicative of vertebral fracture. Osteoporosis occurs in both males and females but is most common among women following the menopause, when bone turnover increases and the rate of bone resorprtion exceeds that of bone formation. These changes result in progressive bone loss and lead to osteoporosis in a significant proportion of women over age 50. Fractures, usually of the spine, hip, and wrist, are the common consequences. From age 50 to age 90, the risk of hip fracture in women increases 50-fold and the risk of vertebral fracture 15- to 30-fold. It is estimated that approximately 40% of 50-year-old women will sustain one or more osteoporosis-related fractures of the spine, hip, or wrist during their remaining lifetimes. Hip fractures, in particular, are associated with substantial morbidity, disability, and mortality.

Paget's Disease is a chronic, focal skeletal disorder characterized by greatly increased and disorderly bone remodeling. Excessive osteoclastic bone resorption is followed by osteoblastic new bone formation, leading to the replacement of the normal bone architecture by disorganized, enlarged, and weakened bone structure.

Clinical manifestations of Paget's disease range from no symptoms to severe morbidity due to bone pain, bone deformity, pathological fractures, and neurological and other complications. Serum alkaline phosphatase, the most frequently used biochemical index of disease activity, provides an objective measure of disease severity and response to therapy.

Alendronate sodium is a suggested treatment in osteoporosis and Paget's disease Alendronate sodium decreases the rate of bone resorption directly, which leads to an indirect decrease in bone formation. In clinical trials, alendronate sodium 40 mg once daily for six months produced highly significant decreases in serum alkaline phosphotase as well as in urinary markers of bone collagen degradation. As a result of the inhibition of bone resorption, alendronate sodium induced generally mild, transient, decreases in serum calcium phosphate. The reduction in serum phosphate may reflect not only the positive bone mineral balance due to alendronate sodium but also a decrease in renal phosphate reabsorption.

Alendronate sodium specifically inhibits Osteoclast-mediated bone resorption thereby preventing resorption. Its mode of action is suggested as follows: At the cellular level, alendronate shows preferential localization to bone resorption sites, specifically under osteoclasts. The osteoclasts adhere normally to the bone surface but lack the ruffled border that is indicative of active resorption. Alendronate does not interfere with osteoclastic recruitment or attachment, but it does inhibit osteoclast activity. Bones examined 6 and 49 days after alendronate administration in rats and mice, respectively, showed that normal bone was formed on top of the alendronate, which was incorporated inside the matrix. While incorporated in bone matrix, alendronate is not pharmacologically active. Thus, alendronate must be continuously administered to suppress osteoclasts on newly formed resorption surfaces. Histomorphometry in baboons and rats showed that alendronate treatment reduces bone turnover. In addition, bone formation exceeds bone resorption at these remodeling sites, leading to progressive gains in bone mass.

For the treatment of osteoporosis, the recommended daily dose is 10 mg. For the prevention of osteoporosis the recommended dose is 5 mg daily. And for the treatment of Paget's disease the dose recommended is 40 mg daily for 6 months.

The Pharmacokinetics of alendronate sodium is as follows:

Relative to an intravenous (IV) reference dose, the mean oral bioavailability in women was 0.7% for conventionally available doses ranging from 5 to 40 mg when administered after an overnight fast and two hours before a standardized breakfast. Oral bioavailability of the 10 mg tablet in men (0.59%) was similar to that in women (0.78%) when administered after an overnight fast and 2 hours before breakfast.

Bioavailability is decreased (by approximately 40%) when 10 mg alendronate was administered either 0.5 or 1 hour before a standardized breakfast, when compared to dosing 2 hours before eating. In studies of treatment and prevention of osteoporosis, alendronate was effective when administered at least 30 minutes before breakfast.

Bioavailability is negligible whether alendronate is administered with or up to two hours after a standardized breakfast. Simultaneous administration of alendronate with coffee or orange juice reduces bioavailability by approximately 60%.

Alendronate transiently distributes to soft tissues following 1 mg/kg IV administration but is then rapidly redistributed to bone or excreted in the urine. The mean steady-state volume of distribution, exclusive of bone, is at least 28:1 in humans. Concentrations of drug in plasma following therapeutic oral doses are too low (less than 5 mg/ml) for analytical detection. Protein binding in human plasma is approximately 78%.

Daily oral doses of alendronate sodium 5, 20, and 40 mg for six weeks) in postmenopausal women produce biochemical changes indicative of dose-dependent inhibition of bone resorption, including decreases in urinary calcium and urinary markers of bone collagen degradation (such as deoxypyridinoline and cross-linked N-telopeptides of type 1 collagen). These biochemical changes tended to return toward baseline values as early as 3 weeks following the discontinuation of therapy.

In the existing mode of delivery, a particular limitation with the delivery of this drug is that there is fear of the drug sticking and causing deterioration to the gastrooesophagal mucous linings of the esophagus with the possibility of ulceration and bleeding. Esophageal adverse experiences, such as esophagitis, esophageal ulcers and erosions have been reported presented with dysphagia, odynophagia or retrostemal pain.

The risk of severe oesophageal adverse experiences appears to be greater in patients who lie down after taking alendronate sodium and/or who fail to swallow it with a full glass of water. Therefore, it is very important that the full dosing instructions are provided to, and understood by, the patient because of possible irritant effects on the upper gastrointestinal mucosa, caution must hitherto be used when alendronate sodium is given to patients with active upper gastrointestinal problems, such as dysphagia, oesophageal diseases, gastritis, duodenitis, or ulcers.

The fear of adherence of the tablet to the esophagus calls for the tablet administration compulsorily with a glass of water.

Disintegration in the oesophagus or stomach causes moderate annoying side effects. The most frequently reported side effects include diarrhea or constipation, headache, stomach gas or fullness, nausea, changes in taste, and muscle pain. More serious side effects include stomach pain, heartburn, pain or difficulty swallowing, black or tarry stools, skin rash, itching (hives) and facial swelling. Signs of a possible allergic reaction are rash, swelling, and difficulty breathing.

The instructions to the patient are that he/she should sit erect or keep walking.

Specific instructions given to patient taking alendronate sodium are as follows:
1. After getting up for the day, swallow alendronate sodium tablet with a full glass 250 ml of water.
2. After swallowing alendronate sodium tablet do not lie down—stay upright (sitting or standing) for at least 30 minutes and until after your first food of the day. This will help the tablet reach the stomach quickly and help avoid irritation of your esophagus.
3. After swallowing the tablet, wait at least 30 minutes before taking the first food, beverage, or other medications. Alendronate sodium must be taken on a totally empty stomach.
4. Do not take alendronate sodium at bedtime or before getting up for the day.

An object of this invention is to provide a delivery vehicle for the drug where there is no fear of the tablet adhering to the walls of the esophagus and at the same time the drug is released in the stomach or in the duodenum area.

Another object of this invention is to enable the drug to be taken even by a patient with oesophageal problems.

Still another object of this invention is to permit the patient to take the drug even at the time of going to bed and independent of the food intake.

Still another object of the invention is to permit a patient to take the drug along with any normal food or drink including fruit juices.

According to this invention there is provided an oral composition in tablet form containing therapeutic amounts of alendronate sodium for release of the alendronate sodium in the stomach and by passing the oesophagus, comprising a compacted granulated core with the alendronate sodium embedded in a hydroxypropyl methyl cellulosic matrix, lined with a moisture barrier film and enclosed in a sugar based inert fiber shell.

Therefore the object of this invention is achieved by imbedding the drug in a hydrophillic hydroxy propyl methyl cellulose matrix, and forming a shell around the core tablet with a sugar in an inert fiber matrix.

In accordance with a process of this invention, there is no fear of adherence to esophagus. The drug is released directly into the stomach (the site of absorption) and the swallowing of the tablets is made much simpler and no postural restrictions are required any longer. The formulation is modified to release the drug at the site of absorption. The hydrophilic matrix and the sugar inert fiber shell used impart the above characteristics.

In accordance with the process of this invention, predetermined quantities of alendronate sodium is sifted and mixed with sifted hydroxy propyl methyl cellulose, lactose and maize starch in a planetary mixer and the mixing is done at slow speed [13 to 26 r.p.m.] for 0 to 20 minutes.

Separately a homogenous smooth paste is made with maize starch blended in purified cold water and mixed in purified hot water above 80 degrees Celsius. The smooth paste is cooled to around 55 degrees Celsius and is poured into the planetary mixture containing the alendronate sodium and the mixture is mixed at a slow speed [13 to 26 r.p.m.] to obtain uniform dough. The wet uniform dough is passed through a multimill having a 10-mesh screen to obtain granules. The granules are dried typically in a fluidized bed dryer for 60 to 120 minutes at temperature ranging between 50 to 70 degrees Celsius or in a tray drier.

The dried granules are sifted on a Vibrosifter to ensure that alendronate embedded-granules pass through 20-mesh sieve. Oversized granules are passed back to the multimill for size reduction. The sifted dried granules are lubricated in the planetary mixer by applying a lubrication coating of a stearate typically magnesium stearate.

The lubricated granules are then taken up for compression in a tablet compression machine to obtain compressed core tablets.

The compressed core tablets are transferred to a coating pan where the core tablets are coated with a multiply moisture barrier film coat, typically of shellac or combination of ethyl cellulose, shellac and ethyl cellulose etc.

The core tablets coated with the moisture barrier film coating are then taken up for sugar shell formation around the core tablets.

As a first step to core formation, a primer coat of dilute sugar solution is applied on the moisture barrier film coated core tablets. The coating is done in a coating pan and after each coat of the primer; talc is sprinkled over the tablets. After the application of primer coat, the primer coat applied tablets are dried with the help of a blower.

A sugar-based shell is formed over the primer-coated tablets in a coating pan. The shell material consists of a mixture containing filtered sugar solution, a cellulose based matrix such as of carboxy methyl cellulose, methyl cellulose, ethyl hydroxy cellulose, a glossing agent, a surfactant for decreasing surface tension and improving blending, a plasticizer such as polyethylene glycol for improving the elasticity of the matrix, a binder such as Polyvinyl pyrolidine, gelatin, gum acacia for binding the sugar molecules with the inert fiber matrix, a smoothener, a glidant and lubricant such as talc and colloidal silicon dioxide. The mixture is homogenized by stirring for at least 30 minutes at speeds ranging from 1000 to 5000 r.p.m. And the shell material is introduced in the coating pan and the material is coated on the primer coated tablets by rotating the pan, sprinkling talc and drying the tablets after each coat with a hot air blower. Typically thirty such coats of the shell material are applied on the tablets.

The sugar coatings of the shell material prevent the disintegration of the tablet until the tablet reaches the stomach linings. The moisture barrier layer also prevents any form of moisture from reaching the core tablets ensuring that the core tablet remains intact until the tablet has settled in the stomach linings.

The sugar based shell and the moisture barrier film coating ensure that there is absolute no contact between alendronate sodium and the oesophageal lining.

The invention will now be described with reference to the accompanying Examples:

EXAMPLE 1

Dry Mixing

The following materials were sifted through a vibrosifter using respective sieves and transferred to the bowl of a planetary mixer.

| Alendronate Sodium | I.P | 1.306 kgs, | 20 # |
|---|---|---|---|
| Microcrystalline Cellulose | I.P. | 0.567 kgs | |
| Lactose | I.P. | 9.100 kgs | |
| Starch | I.P. | 3.827 kgs | |

The mixture was mixed in the planetary mixer for 10 minutes at slow speed.

Granulation

Preparation of Starch paste: A starch paste was prepared using the following:

Starch (Maize) 0.500 kgs

Purified Cold Water 0.600 liters.

Purified Hot Water 2.400 liters.

Wet Mixing: the Starch paste was cooled up to 550 C and added to the bowl of planetary mixer of and mixed at slow speed for 10 minutes till the uniform dough mass was formed. The wet mass was passed on multimill fitted with 10 mm screen. The milled wet granules were dried between 55° C.–60° C. in FBD for about 100 minutes. The loss on drying was. In-Process Control: LOD at 105° C. (I.R. Moisture Balance): 2.0%±0.5%.

Yield: Weight of dried granules was the dried granules were sifted through 20 mesh on vibrosifter and oversized granules through 1.5 mm sieve on multimill at a speed of. The sifted and milled granules were transferred to the planetary mixer for lubrication. Talcum 0.200 kgs, Magnesium Stearate 0.200 kgs, and Methocel K15M 0.500 kgs, were sifted and transferred to a Vibrosifter using 60 # sieves. The dried sifted granules were transferred to a planetary mixer and Talcum and Methocel were added and the mixture was mixed for 5 minutes. The Magnesium Stearate was then transferred and again mixed for 5 minutes.

The granules were taken for compression into core tablets in a temperature of 25 degrees Celsius and humidity below 60%

The compression machine was set up with 7.0 mm deep curvature punches and the compression was started by setting up the parameters of tablets (cores) as under:

Avg. Weight: 161 mg/tab ± 2% w/w
Weight Variation: ± 5% of average weight
Hardness: NLT 3 kg/cm$^2$
Thickness: 3.0 mm
Diameter: 7 mm ± 1.0 mm, D/C Punches
Friability: NMT 1% w/w after 100 rotation (25 rpm)
D.T.: Not less than 15 minutes
Recovering the initial rejection immediately.

The following parameters were monitored during compression by periodical checking of tablets. Maintain the records of results.

1. Avg. weight of tablets & Wt. variation
2. Dimensions
3. Hardness/Friability
4. Disintegration Time Yield: Theoretical Yield: 98% by weight.

The tablets were checked for the following defects and the defective tablets were discarded:

1. Broken Tablets

2. Deformed Tablets

3. Tablets showing capping

4. Tablets with black or foreign particles and oily stains. Rejection from 1,2 & 4 were recoverable.

The following parameters of the core tablets were checked and were found to be as follows

| S.No. | Parameters | Release Limit | Control Limit |
|---|---|---|---|
| 01. | Appearance | White, circular, bi-convex uncoated tablets. | White, circular, bi-convex uncoated tablets. |
| 02. | Average Weight | 161 mg (Limit: 157 to 165 mg) | 161 mg (Limit: 157 to 165 mg) |
| 03. | Disintegration Time | N.L.T 15 minutes | N.L.T. 15 minutes |
| 04. | Diameter | 7 mm ± 0.2 mm | 7 mm ± 0.2 mm |
| 05. | Thickness | 3 ± 0.1 mm | 3 ± 0.1 mm |
| 06. | Identification | Positive | Positive |
| 07. | Weight Variation | ±5% of avg. wt. | ±5% of avg. wt. |
| 08. | Assay: | | |
| | Alendronic Acid | 9.5 mg to 11 mg/tab (95%–110% of L.A.) | 9.5 mg to 11 mg/tab (90%–110% of L.A.) |

The tablets were taken for the shell formation process in which 2.780 kg sugar was dissolved in 2 liters. of Purified Water and filtered through nylon cloth. 0.075 kg of Tylose was soaked in 750 ml of Purified Water. 0.019 kg of Carnauba Wax and 0.019 kgs of Polysorbate 80 were heated in a beaker and mixed and added to the sugar solution. with constant stirring and mixed for 15 minutes.

Separately the following materials were added:

| | | |
|---|---|---|
| a) | PEG 1000 powder | 0.550 kg |
| b) | PVP K30 | 0.088 kg |
| c) | Colloidal Silicon Dioxide | 0.190 kg |
| d) | Titanium Dioxide | 0.780 kg |
| e) | Calcium Carbonate | 0.780 kg |
| f) | Talc | 2.480 kgs |

Separately Diluted_sugar_coating_suspension_was_ prepared by dissolving 0.027 kg PVP K30 in 108 ml in Purified Water and 500 ml sugar.

Shellac solution was prepared by mixing 0.050 kg of shellac with Isopropyl Alcohol and sprinkle Talc over the time while rotating core tablet on the pan. Three coats of shellac solution 5% prepared in IPA were applied by coating on the core tablets in a coating pan. 300 ml of diluted sugar coating suspension was then applied as the primer coat and sprinkle Talc over the time. The tablet bed was dried using blower. Three coats of diluted primer coating solution were applied.

300 ml at a time of sugar coating shell suspension was applied to rotating tablets. The pan was made to rotate for drying up of the tablet. Then Talc was applied by sprinkling over the tablets and drying the tablets with blower. 100 ml of coloring suspension was applied to the glossed tablets and rotated for few minutes and the tablets were dried with a cold blower. 5 coats were applied, last 2 coats were applied without using blower and carry out jogging procedure for 30 minutes. The tablets were polished by using canvas polishing pan.

EXAMPLE 2

Dry Mixing

The following materials were sifted through a vibrosifter using respective sieves and transferred to the bowl of a planetary mixer.

| | | |
|---|---|---|
| Alendronate Sodium | I.P. | 1.306 kgs |
| Lactose | I.P. | 13.200 kgs |
| Starch | I.P. | 0.500 kgs |

The mixture was mixed in the planetary mixer for 10 minutes at slow speed.

Granulation

Preparation of Starch paste: A starch paste was prepared using the following:

| | |
|---|---|
| Methocel E 50 | 0.500 kgs |
| Methylene Chloride | 3.000 liters. |
| Isopropyl Alcohol | 3.000 liters. |

Wet Mixing: The Starch paste was added to the bowl of planetary mixer and mixed at slow speed for 10 minutes till the uniform dough mass was formed. The wet mass was passed on multimill fitted with 10 mm screen. The milled wet granules were dried between 40° C.–50° C. in FBD for about 100 minutes. The loss on drying was.

In-Process Control: LOD at 105° C. (I.R. Moisture Balance): 2.0%±0.5%.

Yield: Weight of dried granules was The dried granules were sifted through 20 mesh on vibrosifter and oversized granules through 1.5 mm sieve on multimill at a speed of. The sifted and milled granules were transferred to the planetary mixer for lubrication. Talcum 0.300 kgs, Magnesium Stearate 0.300 kgs were sifted and transferred to a Vibrosifter using sieves. The dried sifted granules were transferred to a planetary mixer and Talcum and Magnesium Stearate were added were mixed for 7 minutes.

The granules were taken for compression into core tablets in a temperature of 25 degrees Celsius and humidity below 60%

The compression machine was set up with 7.0 mm deep curvature punches and the compression was started by setting up the parameters of tablets (cores) as under:

Avg. Weight: 161 mg/tab ± 2% w/w
Weight Variation: ±5% of average weight
Hardness: NLT 3 kg/cm$^2$
Thickness: 3.0 mm
Diameter: 7 mm ± 1.0 mm, D/C Punches
Friability: NMT 1% w/w after 100 rotation (25 rpm)
D.T.: Not less than 15 minutes
Recovering the initial rejection immediately.

The following parameters were monitored during compression by periodical checking of tablets. Maintain the records of results.

| | |
|---|---|
| 1. Avg. weight of tablets & Wt. variation | 3. Hardness/Friability |
| 2. Dimensions | 4. Disintegration Time |

Yield: Theoretical Yield: 98% by weight.

The tablets were checked for the following defects and defective tablets were discarded:

1. Broken Tablets
2. Deformed Tablets
3. Tablets showing capping
4. Tablets with black or foreign particles and oily stains.

Rejection from 1,2 & 4 were recoverable.

The following parameters of the core tablets were checked and were found to be as follows

| S.No. | Parameters | Release Limit | Control Limit |
|---|---|---|---|
| 01. | Appearance | White, circular, bi-convex uncoated tablets. | White, circular, bi-convex uncoated tablets. |
| 02. | Average Weight | 161 mg (Limit: 156 to 165 mg) | 161 mg (Limit: 156 to 165 mg) |
| 03. | Disintegration Time | N.M.T 15 minutes | N.M.T. 15 minutes |
| 04. | Diameter | 7 mm ± 0.1 mm | 7 mm ± 0.1 mm |
| 05. | Thickness | 3 ± 0.2 mm | 3 ± 0.2 mm |
| 06. | Identification | Positive | Positive |
| 07. | Weight Variation | ±5% of avg. wt. | ±5% of avg. wt. |
| 08. | Assay: | | |
| | Alendronic Acid | 9.5 mg to 11 mg/tab (95%–110% of L.A.) | 9.5 mg to 11 mg/tab (90%–110% of L.A.) |

The tablets were taken for the shell formation process in which 2.780 kg sugar was dissolved in 2 liters. of Purified Water and filtered through nylon cloth. 0.075 kg of Tylose was soaked in 750 ml of Purified Water. 0.010 kg of Carnauba Wax and 0.019 kgs of Polysorbate 80 were heated in a beaker and mixed and added to the sugar solution. with constant stirring and mixed for 15 minutes.

Separately the following materials were added:

| a) | Gum acacia | 0.067 kg |
|----|------------|----------|
| b) | Gelatin | 0.097 kg |
| c) | Titanium Dioxide | 0.070 kg |
| d) | Calcium Carbonate | 0.078 kg |
| e) | Talc | 1.600 kgs |

Separately Diluted_sugar_coating_suspension_was_ prepared by dissolving 0.027 kg PVP K30 in 108 ml in Purified Water and 500 ml sugar.

Ethyl cellulose solution 3% was prepared in Methylene Chloride and Isopropyl Alcohol (1:2) proportion i.e. Ethyl Cellulose 300 kgs in 660 ml Isopropyl Alcohol and 330 ml Methylene Chloride solution and applied over the core tablets. 300 ml of diluted sugar coating suspension was then applied as the primer coat and sprinkle Talc over the time. The tablet bed was dried using blower. Three coats of diluted primer coating solution was applied.

300 ml at a time of sugar coating shell suspension was applied to rotating tablets. The pan was made to rotate for drying up of the tablet. Then Talc was applied by sprinkling over the tablets and drying the tablets with blower. 100 ml of coloring suspension was applied to the glossed tablets and rotated for few minutes and the tablets were dried with a cold blower. 5 coats were applied, last 2 coats were applied without using blower and carry out jogging procedure for 30 minutes. The tablets were polished by using canvas polishing pan.

EXAMPLE 3

Dry Mixing

The following materials were sifted through a vibrosifter using respective sieves and transferred to the bowl of a planetary mixer.

| Alendronate Sodium | I.P. | 1.306 kgs, | 20 # |
|---|---|---|---|
| Microcrystalline Cellulose | I.P. | 0.400 kgs | |
| Lactose | I.P. | 9.000 kgs | |
| Starch | I.P. | 3.800 kgs | |

Granulation

Preparation of Starch paste: A starch paste was prepared using the following:

| Starch (Maize) | 0.500 kgs |
|---|---|
| Purified Cold Water | 0.600 liters. |
| Purified Hot Water | 2.400 liters. |

Wet Mixing: The Starch paste was cooled up to 55° C. and added to the bowl of planetary mixer of and mixed at slow speed for 10 minutes till the uniform dough mass was formed. The wet mass was passed on multimill fitted with 10 mm screen. The milled wet granules were dried between 55° C.–60° C. in FBD for about 100 minutes. The loss on drying was.

In-Process Control: LOD at 105° C. (I.R. Moisture Balance): 2.0%±0.5%.

Yield: Weight of dried granules was The dried granules were sifted through 20 mesh on vibrosifter and oversized granules through 1.5 mm sieve on multimill at a speed of. The sifted and milled granules were transferred to the planetary mixer for lubrication. Talcum 0.300 kg, Magnesium Stearate 0.200 kg, and Methocel K100M CR Premium EP 0.600 kg, were sifted and transferred to a Vibrosifter using sieves. The dried sifted granules were transferred to a planetary mixer and Talcum and Methocel were added and the mixture was mixed for 5 minutes. The Magnesium Stearate was then transferred and again mixed for 5 minutes.

The granules were taken for compression into core tablets in a temperature of 25 degrees Celsius and humidity below 60%

The compression machine was set up with 7.0 mm deep curvature punches and the compression was started by setting up the parameters of tablets (cores) as under:

Avg. Weight: 161 mg/tab ± 2% w/w
Weight Variation: ±5% of average weight
Hardness: NLT 3 kg/cm$^2$
Thickness: 3.0 mm
Diameter: 7 mm ± 1.0 mm, D/C punches
Friability: NMT 1% w/w after 100 rotation (25 rpm)
D.T.: Not less than 15 minutes
Recovering the initial rejection immediately.

The following parameters were monitored during compression by periodical checking of tablets. Maintain the records of results.

1. Avg. weight of tablets & Wt. variation   3. Hardness/Friability
2. Dimensions   4. Disintegration Time Yield: Theoretical Yield: 98% by weight The tablets were checked and defective tablets were discarded:
1. Broken Tablets
2. Deformed Tablets
3. Tablets showing capping
4. Tablets with black or foreign particles and oily stains.

Rejection from 1,2 & 4 were recoverable.

The following parameters of the core tablets were checked and were found to be as follows

| S.No. | Parameters | Release Limit | Control Limit |
|---|---|---|---|
| 01. | Appearance | White, circular; biconvex uncoated tablets. | White, circular, biconvex uncoated tablets. |
| 02. | Average Weight | 161 mg (Limit: 156 to 165 mg) | 161 mg (Limit: 156 to 165 mg) |
| 03. | Disintegration Time | N.L.T 15 minutes | N.L.T. 15 minutes |
| 04. | Thickness | 3.0 mm | 3.0 mm |
| 05. | Identification | Positive | Positive |
| 06. | Weight Variation | ±5% of avg. wt. | ±5% of avg. wt. |
| 07. | Assay Alendronic Acid | 9.5 mg to 11 mg/tab (95%–110% of L.A.) | 9.5 mg to 11 mg/tab (90%–110% of L.A.) |

The tablets were taken for the shell formation process in which 2.780 kg sugar was dissolved in 2 liters. of Purified Water and filtered through nylon cloth. 0.075 kg of Tylose was soaked in 750 ml of Purified Water. 0.019 kg of Carnauba Wax and 0.019 kgs of Polysorbate 80 were heated in a beaker and mixed and added to the sugar solution. with constant stirring and mixed for 15 minutes.

| a) | PEG 1000 powder | 0.550 kg |
|---|---|---|
| b) | PVP K30 | 0.088 kg |
| c) | Colloidal Silicon Dioxide | 0.190 kg |
| d) | Titanium Dioxide | 0.780 kg |
| e) | Calcium Carbonate | 0.780 kg |
| f) | Talc | 2.480 kgs |

Separately Diluted_sugar_coating_suspension_was_ prepared by dissolving 0.027 kg PVP K30 in 108 ml in Purified Water and 500 ml sugar.

Shellac solution was prepared by mixing 0.050 kg of shellac with Isopropyl Alcohol and sprinkle Talc over the time while rotating core tablet on the pan. Three coats of shellac solution 5% prepared in IPA were applied by coating on the core tablets in a coating pan. 300 ml of diluted sugar coating suspension was then applied as the primer coat and sprinkle Talc over the time. The tablet bed was dried using blower. Three coats of diluted primer coating solution was applied.

300 ml at a time of sugar coating shell suspension was applied to rotating tablets. The pan was made to rotate for drying up of the tablet. Then Talc was applied by sprinkling over the tablets and drying the tablets with blower. 100 ml of coloring suspension was applied to the glossed tablets and rotated for few minutes and the tablets were dried with a cold blower. 5 coats were applied, last 2 coats were applied without using blower and carry out jogging procedure for 30 minutes. The tablets were polished by using canvas polishing pan.

EXAMPLE 4

Dry Mixing

The following materials were sifted through a vibrosifter using respective sieves and transferred to the bowl of a planetary mixer.

| Alendronate Sodium | I.P. | 1.306 kgs, | 20 # |
|---|---|---|---|
| Microcrystalline Cellulose | I.P. | 0.567 kgs | |
| Lactose | I.P. | 9.000 kgs | |
| Starch | I.P. | 3.800 kgs | |

The mixture was mixed in the planetary mixer for 10 minutes at slow speed.

Granulation

Preparation of Starch paste: A starch paste was prepared using the following:

Starch (Maize) 0.500 kgs

Purified Cold Water 0.600 liters.

Purified Hot Water 2.400 liters.

Wet Mixing: the Starch paste was cooled up to 55° C. and added to the bowl of planetary mixer of and mixed at slow speed for 10 minutes till the uniform dough mass was formed. The wet mass was passed on multimill fitted with 10 mm screen. The milled wet granules were dried between 55° C.–60° C. in FBD for about 100 minutes. The loss on drying was.

In-Process Control: LOD at 105° C. (I.R. Moisture Balance): 2.0%±0.5%.

Yield: Weight of dried granules was The dried granules were sifted through 20 mesh on vibrosifter and oversized granules through 1.5 mm sieve on multimill at a speed of. The sifted and milled granules were transferred to the planetary mixer for lubrication. Talcum 0.300 kg, Magnesium Stearate 0.300 kg, and Methocel K4M 0.600 kg, were sifted and transferred to a Vibrosifter using sieves. The dried sifted granules were transferred to a planetary mixer and Talcum and Methocel were added and the mixture was mixed for 5 minutes. The Magnesium Stearate was then transferred and again mixed for 5 minutes.

The granules were taken for compression into core tablets in a temperature of 25 degrees Celsius and humidity below 60%

The compression machine was set up with 7.0 mm deep curvature punches and the compression was started by setting up the parameters of tablets (cores) as under:

Avg. Weight: 161 mg/tab ± 2% w/w
Weight Variation: ±5% of average weight
Hardness: NLT 3 kg/cm$^2$
Thickness: 3.0 mm
Diameter: 7 mm ± 1.0 mm, S/C punches
Friability: NMT 1% w/w after 100 rotation (25 rpm)
D.T.: Not less than 15 minutes
Recovering the initial rejection immediately.

The following parameters were monitored during compression by periodical checking of tablets. Maintain the records of results.

| 1. Avg. weight of tablets & Wt. variation | 3. Hardness/Friability |
|---|---|
| 2. Dimensions | 4. Disintegration Time |

Yield: Theoretical Yield: 98% by weight

The tablets were checked and the defective tablets were discarded:

1. Broken Tablets
2. Deformed Tablets
3. Tablets showing capping
4. Tablets with black or foreign particles and oily stains.

Rejection from 1,2 & 4 were recoverable.

The following parameters of the core tablets were checked and were found to be as follows

| S.No. | Parameters | Release Limit | Control Limit |
|---|---|---|---|
| 01. | Appearance | White, circular; biconvex uncoated tablets. | White, circular, biconvex uncoated tablets. |
| 02. | Average Weight | 161 mg (Limit: 157 to 165 mg) | 161 mg (Limit: 157 to 165 mg) |
| 03. | Disintegration Time | N.L.T 15 minutes | N.L.T. 15 minutes |
| 04. | Diameter | 7 mm ± 0.2 mm | 7 mm ± 0.2 mm |
| 05. | Thickness | 3.0 mm | 3.0 mm |
| 06. | Identification | Positive | Positive |
| 07. | Weight Variation | ±5% of avg. wt. | ±5% of avg. wt. |

-continued

| S.No. | Parameters | Release Limit | Control Limit |
|---|---|---|---|
| 08. | Assay: Alendronic Acid | 9.5 mg to 11 mg/tab (95%–110% of L.A.) | 9.5 mg to 11 mg/tab (90%–110% of L.A.) |

The tablets were taken for the shell formation process in which 2.780 kg sugar was dissolved in 2 liters. of Purified Water and filtered through nylon cloth. 0.075 kg of Tylose was soaked in 750 ml of Purified Water. 0.019 kg of Carnauba Wax and 0.019 kgs of Polysorbate 80 were heated in a beaker and mixed and added to the sugar solution. with constant stirring and mixed for 15 minutes.

Separately the following materials were added:

| a) | PEG 1000 powder | 0.550 kg |
|---|---|---|
| b) | PVP K30 | 0.088 kg |
| c) | Colloidal Silicon Dioxide | 0.190 kg |
| d) | Titanium Dioxide | 0.780 kg |
| e) | Calcium Carbonate | 0.780 kg |
| f) | Talc | 2.480 kgs | and homogenized by stirring for 30 minutes.

Separately Diluted_sugar_coating_suspension_was_ prepared by dissolving 0.027 kg PVP K30 in 108 ml in Purified Water and 500 ml sugar.

Shellac solution was prepared by mixing 0.050 kg of shellac with Isopropyl Alcohol and sprinkle Talc over the time while rotating core tablet on the pan. Three coats of shellac solution 20% prepared in IPA were applied by coating on the core tablets in a coating pan. 300 ml of diluted sugar coating suspension was then applied as the primer coat and sprinkle Talc over the time. The tablet bed was dried using blower. Three coats of diluted primer coating solution was applied.

300 ml at a time of sugar coating shell suspension was applied to rotating tablets. The pan was made to rotate for drying up of the tablet. Then Talc was applied by sprinkling over the tablets and drying the tablets with blower. 100 ml of coloring suspension was applied to the glossed tablets and rotated for few minutes and the tablets were dried with a cold blower. 5 coats were applied, last 2 coats were applied without using blower and carry out jogging procedure for 30 minutes. The tablets were polished by using canvas polishing pan.

EXAMPLE 6

Dry Mixing

The following materials were sifted through a vibrosifter using respective sieves and transferred to the bowl of a planetary mixer.

| Alendronate Sodium | I.P. | 1.306 kgs, | 20 # |
|---|---|---|---|
| Microcrystalline Cellulose | I.P. | 0.400 kgs | |
| Lactose | I.P. | 9.000 kgs | |
| Starch | I.P. | 3.800 kgs | |

The mixture was mixed in the planetary mixer for 10 minutes at slow speed.

Granulation

Preparation of Starch paste: A starch paste was prepared using the following:

Starch (Maize) 0.500 kgs

Purified Cold Water 0.600 liters.

Purified Hot Water 2.400 liters.

Wet Mixing: the Starch paste was cooled up to 55° C. and added to the bowl of planetary mixer of and mixed at slow speed for 10 minutes till the uniform dough mass was formed. The wet mass was passed on multimill fitted with 10 mm screen. The milled wet granules were dried between 55° C.–60° C. in FBD for about 100 minutes. The loss on drying was.

In-Process Control: LOD at 105° C. (I.R. Moisture Balance): 2.0%±0.5%.

Yield: Weight of dried granules was The dried granules were sifted through 20 mesh on vibrosifter and oversized granules through 1.5 mm sieve on multimill at a speed of. The sifted and milled granules were transferred to the planetary mixer for lubrication. Talcum 0.300 kg, Magnesium Stearate 0.300 kg, and Guar gum 0.600 kg, were sifted and transferred to a Vibrosifter using sieves. The dried sifted granules were transferred to a planetary mixer and Talcum and Methocel were added and the mixture was mixed for 5 minutes. The Magnesium Stearate was then transferred and again mixed for 5 minutes.

The granules were taken for compression into core tablets in a temperature of 25 degrees Celsius and humidity below 60%

The compression machine was set up with 7.0 mm deep curvature punches and the compression was started by setting up the parameters of tablets (cores) as under:

Avg. Weight: 161 mg/tab ± 2% w/w
Weight Variation: ±5% of average weight
Hardness: NLT 3 kg/cm$^2$
Thickness: 3.0 mm
Diameter: 7 mm ± 1.0 mm, D/C punches
Friability: NMT 1% w/w after 100 rotation (25 rpm)
D.T.: Not less than 15 minutes The following parameters were monitored during compression by periodical checking of tablets. Maintain the records of results.

1. Avg. weight of tablets & Wt. variation
2. Dimensions
3. Hardness/Friability
4. Disintegration Time Yield: Theoretical Yield: 98% by weight.

The tablets were checked and the defective tablets were discarded:

1. Broken Tablets
2. Deformed Tablets
3. Tablets showing capping
4. Tablets with black or foreign particles and oily stains.

Rejection from 1,2 & 4 were recoverable.

The following parameters of the core tablets were checked and were found to be as follows

| S.No. | Parameters | Release Limit | Control Limit |
|---|---|---|---|
| 01. | Appearance | White, circular; bi-convex uncoated tablets. | White, circular, bi-convex uncoated tablets. |

-continued

| S.No. | Parameters | Release Limit | Control Limit |
|---|---|---|---|
| 02. | Average Weight | 161 mg (Limit: 157 to 165 mg) | 161 mg (Limit: 157 to 165 mg) |
| 03. | Disintegration Time | N.L.T 25 minutes | N.L.T. 30 minutes |
| 04. | Diameter | 7 mm ± 0.2 mm | 7 mm ± 0.2 mm |
| 05. | Thickness | 3 ± 0.2 mm | 3 ± 0.2 mm |
| 06. | Identification | Positive | Positive |
| 07. | Weight Variation | ±5% of avg. wt. | ±5% of avg. wt. |
| 08. | Assay: Alendronic Acid | 9.5 mg to 11 mg/tab (95%–110% of L.A.) | 9.5 mg to 11 mg/tab (90%–110% of L.A.) |

The tablets were taken for the shell formation process in which 2.780 kg sugar was dissolved in 2 liters. of Purified Water and filtered through nylon cloth.

0.075 kg of Tylose was soaked in 750 ml of Purified Water. 0.019 kg of Carnauba Wax and 0.019 kgs of Polysorbate 80 were heated in a beaker and mixed and added to the sugar solution. with constant stirring and mixed for 15 minutes.

| a) | PEG 1000 powder | 0.550 kg |
|---|---|---|
| b) | PVP K30 | 0.088 kg |
| c) | Colloidal Silicon Dioxide | 0.190 kg |
| d) | Titanium Dioxide | 0.780 kg |
| e) | Calcium Carbonate | 0.780 kg |
| f) | Talc | 2.480 kgs |

Separately Diluted_sugar_coating_suspension_was_ prepared by dissolving 0.027 kg PVP K30 in 108 ml in Purified Water and 500 ml sugar.

Shellac solution was prepared by mixing 0.050 kg of shellac with Isopropyl Alcohol and sprinkle Talc over the time while rotating core tablet on the pan. Three coats of shellac solution 5% prepared in IPA were applied by coating on the core tablets in a coating pan. 300 ml of diluted sugar coating suspension was then applied as the primer coat and sprinkle Talc over the time. The tablet bed was dried using blower. Three coats of diluted primer coating solution was applied.

300 ml at a time of sugar coating shell suspension was applied to rotating tablets. The pan was made to rotate for drying up of the tablet. Then Talc was applied by sprinkling over the tablets and drying the tablets with blower. 100 ml of coloring suspension was applied to the glossed tablets and rotated for few minutes and the tablets were dried with a cold blower. 5 coats were applied, last 2 coats were applied without using blower and carry out jogging procedure for 30 minutes. The tablets were polished by using canvas polishing pan.

The invention will now be described with reference to the following Trials:

Trials

Anecdote 1

A middle aged lady was recommended Alendronate Sodium 10 mg Tablets every morning with 200 ml of water 30 minutes before intake of first food. The patient had the complaint of low bone mass including those of hip and spine. On taking the Alendronate Sodium 10 mg Tablets of the prior art, the patient presented herself with esophageal distress symptoms including, nausea and vomiting. The patient experienced esophageal reaction even when precaution for use was followed. The patient changed to the Alendronate Sodium 10 mg in accordance with this invention. All the adverse symptoms were eliminated.

Anecdote 2

A lady aged 44 years suffering from low bone density mass and having oesophageal distress was prescribed Alendronate Sodium 10 mg tablets twice a day. She reported acute oesophagitis with severe burning and occasional vomiting. The distress was so acute that there was poor patient compliance. The lady was given the tablets in accordance with this invention. She was able to consume these tablets with ease with no distress and good compliance.

Anecdote 3

A lady having Paget's disease of bone ostetitis deformation which is characterized by excessive and disorganized bone resorption and formation was prescribed treatment with Alendronate Sodium 10 mg Tablets. The patient reported side effects such as abdominal pain, oesophageal ulcer, vomiting. She was administered the tablets in accordance with this invention daily in the morning with 200 ml of water, no abnormal esophageal pain was reported and nausea condition was not found. The administration of the Alendronate Sodium Tablets in accordance with this invention minimizes the oesophageal reaction.

Anecdotal 3

A post menopausal lady 50 years of age diagnosed with osteoporosis characterized by low bone mass and micro architectural deterioration of bone tissue, leading to enhanced bone fragility bones on treatment of Alendronate Sodium Tablets change the bone mass density and present the fragility factures of bone. which not only prevents the loss of bone but actually helps to rebuild bone and makes the bone less likely to fracture. The patient had to swallow Alendronate Sodium 10 mg Tablets with a full glass of plain water and no mineral water, milk, tea, coffee and juice. After taking the medicine the patient had to sit erect for 30 minutes and until first food of the day. On administration of Alendronate Sodium Tablets oesophageal reflux, oesophageal ulceration was reported by the patient. However, on administration of Alendronate Sodium Tablets in accordance with this invention such problems were overcome and the patient need not sit erect or walk for half an hour after administration of the tablet.

Anecdotal 4

A 65 years old lay diagnosed with brittle bones and suffered a hip fracture. She was bed ridden. The patient was given the treatment of Alendronate Sodium Tablets to increase the bone mass density of the spine, hip and total body in postmenopausal woman with osteoporosis. The adverse effects reported were nausea, headache, acid regurgitation. It was not possible for her to take the tablet in the prone position. But changing to Alendronate Sodium Tablets sugar coated in accordance with this invention removed all the adverse effects and the patient could take the medication were eliminated.

Anecdotal 5

A male 45 years having suffered rickets in child hood and with low bone density mass developed osteomalacia, bone matrix resulting in soft bone and rickets and teeth defects and muscle hypotoriza. The patient was prescribed Alendronate Sodium 10 mg Tablets. Some gastro intestinal disturbances like abdominal pain, nausea, vomiting and diarrhea was reported. But after changing to sugar coated Alendronate Sodium 10 mg Tablets in accordance with this invention such disturbances was not reported.

While emphasis has been placed herein on the structure of the tablet in the process of manufacture thereof it will be appreciated that many embodiments can be made and that many changes can be made in the preferred embodiments without departing from the principals of the invention. These and other changes in the preferred embodiment as well as other embodiments of the invention will be apparent to those skilled in the art from the disclosure herein, whereby it is to be distinctly understood that the foregoing descriptive matter is to be interpreted merely as illustrative of the invention and not as a limitation.

What is claimed is:

1. An oral composition in tablet form containing therapeutic amounts of alendronate sodium for release of the alendronate sodium in the stomach and by passing the oesophagus, comprising a compacted granulated core with the alendronate sodium embedded in an inert fiber matrix, coated with a moisture barrier film and enclosed in a sugar based inert fiber matrix shell, wherein the inert fiber matrix comprises a mixture of hydroxy propyl methyl cellulose and excipient, and wherein the moisture barrier film comprises a mixture of shellac and ethyl cellulose.

2. An oral composition in tablet form containing therapeutic amounts of alendronate sodium as claimed in claim 1, in which the sugar based inert fiber matrix shell contains carboxy methyl cellulose.

* * * * *